(12) United States Patent
Bernhardi et al.

(10) Patent No.: US 7,050,912 B2
(45) Date of Patent: *May 23, 2006

(54) METHOD OF DETERMINING THE ELASTOPLASTIC BEHAVIOR OF COMPONENTS CONSISTING OF ANISOTROPIC MATERIAL AND USE OF THE METHOD

(75) Inventors: Otto Bernhardi, Bad Schoenborn (DE); Roland Muecke, Windisch (CH)

(73) Assignee: ALSTOM Technology Ltd., Baden (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/935,167

(22) Filed: Sep. 8, 2004

(65) Prior Publication Data

US 2005/0065749 A1     Mar. 24, 2005

Related U.S. Application Data

(63) Continuation of application No. PCT/CH03/00135, filed on Feb. 21, 2003.

(30) Foreign Application Priority Data

Mar. 8, 2002 (CH) .............................. 2002 0402/02

(51) Int. Cl.
- *G01L 1/00* (2006.01)
- *G01L 3/00* (2006.01)
- *G01L 5/00* (2006.01)
- *G06F 19/00* (2006.01)

(52) U.S. Cl. .......................................... 702/42; 73/760
(58) Field of Classification Search ...................... None
See application file for complete search history.

(56) References Cited

U.S. PATENT DOCUMENTS

| 5,736,645 | A | 4/1998 | Chin-Chan et al. |
| 6,715,364 | B1 * | 4/2004 | Bernhardi et al. ............ 73/789 |

FOREIGN PATENT DOCUMENTS

| DE | 101 18 542 A1 | 10/2002 |
| EP | 1 249 694 A2 | 10/2002 |
| WO | 03/076908 A1 | 9/2003 |

OTHER PUBLICATIONS

Search Report from CH 0402/02 (Jul. 4, 2002).
Search Report from PCT/CH03/00135 (Jul. 4, 2003).
Ramberg, Walter, William R. Osgood. "Description of stress-strain curves by three parameters." National advisory committee for aeronautics. Technical note No. 902.
Tsao, T. P. et al., "Long term effect of power system unbalance on the corrosion fatigue life expenditure of low pressure turbine blades." IEE Proc.—Sci. Meas. Technol., vol. 147, No. 5, Sep. 2000 (IEE).
Compendex abstract of Ekh, Magnus. "Modeling of inelastic response of metals with emphasis on cyclic viscoplasticity." Engineering information inc. Nr. 1572, 2000 (Doktorsavh Chalmers Tek Hogsk; Doktorsavhandlingar vid Chalmers Tekniska Hogskola).
Inspec abstract of Vaz, M., D.R.J. Owen. "Aspects of ductile fracture and adaptive mesh refinement in damaged elastoplastic materials." Int. J. Numer. Methods Eng. (UK), International journal for numerical methods in engineering, Jan. 10, 2001, (Wiley).
Compendex abstract of Cligoj, C.C. "Finite deformation coupled thermomechanical problems and generalized standard materials." Int.J. Numer. Methods Eng; International journal for numerical methods in engineering, Jul. 30, 1998, (John Wiley and Sons Ltd, Chichester England).

* cited by examiner

*Primary Examiner*—John Barlow
*Assistant Examiner*—Sujoy Kundu
(74) *Attorney, Agent, or Firm*—Cermak & Kenealy, LLP; Adam J. Cermak

(57) ABSTRACT

A method of determining the elastoplastic behavior of components, in particular of gas turbine plants, at high temperatures. First of all, the linear-elastic behavior is determined and the inelastic behavior is taken into account on the basis of the linear-elastic results by using the Neuber rule, the anisotropic characteristics of the components, as occur in particular through the use of single-crystalline materials, are taken into account in a simple manner by using a modified anistropic Neuber rule in the form $$\sigma^{*2} = \sigma_{ep}^2\left(1 + \frac{A}{C}\frac{\alpha}{E_R}\left(\frac{A\sigma_{ep}^2}{\sigma_0^2}\right)^{n-1}\right)$$

where
A=inelastic anisotropic correction term, $$A = \frac{1}{2}[F(D_{yy} - D_{zz})^2 + G(D_{zz} - D_{xx})^2 + H(D_{xx} - D_{yy})^2 + 2LD_{yz}^2 + 2MD_{zx}^2 + 2ND_{xy}^2]$$

where F, G, H, L, M and N are the Hill constants,
C=elastic anisotropic correction term, $C = \underline{D} \cdot \underline{E}^{-1} \cdot \underline{D}$
$\sigma^*$=determined linear stress,
$\sigma_{ep}$=estimated inelastic stress,
$\underline{D}$=direction vector of the elastic and inelastic stresses
$\underline{E}^{-1}$=inverse stiffness matrix,
$E_R$=reference stiffness,
$\sigma_0$=reference stress, and $\sigma$
$\alpha$, n=material constants.

7 Claims, No Drawings

METHOD OF DETERMINING THE ELASTOPLASTIC BEHAVIOR OF COMPONENTS CONSISTING OF ANISOTROPIC MATERIAL AND USE OF THE METHOD

This application is a Continuation of, and claims priority under 35 U.S.C. § 120 to, International application number PCT/CH03/00135, filed 21 Feb. 2003, and claims priority under 35 U.S.C. § 119 to Swiss application number 2002 0402/02, filed 8 Mar. 2003, the entireties of which are incorporated by reference herein.

BACKGROUND OF THE INVENTION

1. Field of the Invention

The present invention relates to the field of analyzing and predicting the behavior of mechanical components.

2. Brief Description of the Related Art

The components in gas turbines (moving blades, guide blades, liners, etc.) are as a rule so highly stressed that they have only a finite service life. It is necessary to predict this service life for a reliable and economical design of gas turbines.

The loading of the components is composed of forces, high thermal loads, oxidation and corrosion. The mechanical and thermal loading leads in many cases to fatigue of the components after just a few thousand load cycles. This low cycle fatigue is reproduced in the isothermal case by LCF tests (LCF=Low Cycle Fatigue) and in the anisothermal case by TMF tests (TMF=Thermal Mechanical Fatigue).

The stresses caused by the loading are determined in the design phase of the gas turbine. The complexity of the geometry and/or of the loading requires the use of the finite element (FE) method for determining the stresses. However, since inelastic calculations, which are often necessary, are as a rule not possible for reasons of cost and time, the service life prediction is based almost exclusively on linear-elastic stresses. Usually only isothermal data (strain-controlled LCF tests) are available, for which reason anisothermal cycles have to be evaluated with LCF data.

In this case, the amplitude of the total equivalent strain $\epsilon_{v,ep}$ is used as a measure of the damage (damage law). If the requisite number of cycles $N_{req}$ in the component is to be achieved, the amplitude of the total equivalent strain $\epsilon_{v,ep}$ at each location of the component must satisfy the equation $$\epsilon_{v,ep} \leq \epsilon_a^M(T_{dam}, N_{req}) \qquad (a)$$

where $\epsilon_a^M$ is the admissible total strain amplitude which is determined from isothermal LCF tests. It is to be determined for various temperatures and cycle numbers. The temperature $T_{dam}$ which gives rise to this damage be suitably selected for a cycle with varying temperature.

If the decisive loading at high temperatures acts for several minutes, additional damage can be expected. In order to be able to detect the reduced service life on account of the accumulation of damage by creep fatigue and cyclical fatigue, LCF data are obtained from tests with retention time.

The measure of damage $\epsilon_{v,ep}$ corresponds to the strain amplitude of a balanced cycle. This cycle is determined from the cycle analyzed in a linear-elastic manner via a modified Neuber rule:

$$\underline{\sigma}^{*dev} \cdot \underline{\epsilon}^*(\underline{\sigma}^{*dev}) = \underline{\sigma}_{ep}^{dev} \cdot \underline{\epsilon}_{ep}(\underline{\sigma}^{dev}) \qquad (b)$$

where $\underline{\sigma}^{*dev}$ is the vector of the deviator of the linear-elastic stress amplitude $\underline{\epsilon}(\underline{\sigma}^{*dev})$ is the vector of the linear-elastic strain amplitude $\underline{\sigma}_{ep}^{dev}$ is the vector of the deviator of the total elastic-plastic strain amplitude, and $\underline{\epsilon}_{ep}(\underline{\sigma}^{dev})$ is the vector of the elastic-plastic strain amplitude The degree of damage $\epsilon_{v,ep}$ is determined via an equivalent hypothesis from the vector of the total elastic-plastic strain amplitude $\underline{\epsilon}_{ep}(\underline{\sigma}^{dev})$.

The cyclic $\sigma$-$\epsilon$ curve necessary for determining the total elastic-plastic strain amplitude $\underline{\epsilon}_{ep}(\underline{\sigma}^{dev})$ is represented analytically by a modified Ramberg-Osgood equation.

The inelastic effects occurring in gas turbine components (blades, combustion chambers) can then be detected approximately by means of the Neuber rule. These effects have to be taken into account in the service life prediction of the designs. However, only the Neuber rule (b) for materials with isotropic mechanical behavior has been known hitherto.

Since, in gas turbine construction, (anisotropic) single-crystal materials are increasingly used in the components, specifically the turbine blades, on account of their special properties, it would be desirable for the design of the components—in particular with regard to the determination of the service life under cyclic loading—to have a calculation method analogous to the case of isotropic materials.

SUMMARY OF THE INVENTION

It is therefore an object of the invention to specify a method of approximately determining the elastoplastic behavior of single-crystalline materials at high temperatures, which method can be used in particular for determining the service life of components of a gas turbine plant.

An aspect of the present invention, in order to take into account anisotropic characteristics of the components, as occur in particular through the use of single-crystalline materials, includes using a modified anisotropic Neuber rule of the form $$\underline{\sigma}^{*dev} \underline{\epsilon}^*(\underline{\sigma}^{*dev}) = \underline{\sigma}^{*dev} \underline{E}^{-1} \underline{\sigma}^{*dev}$$

$$= \underline{\sigma}_{ep}^{dev} \underline{E}^{-1} \underline{\sigma}_{ep}^{dev} + \underline{\sigma}_{ep}^{dev} \cdot \frac{\partial \sigma_{v,ep}^2}{\partial \underline{\sigma}_{ep}} \cdot \frac{\alpha}{E_R} \left( \frac{\sigma_{v,ep}^2}{\sigma_0^2} \right)^{n-1}$$

In this case, the following equations $$\underline{\sigma}^{*dev} = \underline{D} \sqrt{\sigma^{*2}}$$

and $$\underline{\sigma}_{ep}^{dev} = \underline{D} \sqrt{\sigma_{ep}^2}$$

are used for the quantities $\underline{\sigma}^{*dev}$ and $\underline{\sigma}_{ep}^{dev}$.

Here, $\underline{D} = [D_{xx}, D_{yy}, D_{zz}, D_{yz}, D_{zx}, D_{xy}]$ is a direction vector of the length 1, $\underline{D}^T \underline{D} = 1$, which in addition has deviator characteristics, $D_{xx} + D_{yy} + D_{zz} = 1$. Furthermore, the equations $\underline{\sigma}^* \cdot \underline{\sigma}^* = \sigma^2$ and $\underline{\sigma}_{ep} \cdot \underline{\sigma}_{ep} = \sigma_{ep}^2$ apply, from which the modified Neuber rule can be represented in the form $$\sigma^{*2} = \sigma_{ep}^2 \left( 1 + \frac{A}{C} \frac{\alpha}{E_R} \left( \frac{A\sigma_{ep}^2}{\sigma_0^2} \right)^{n-1} \right)$$

with the anisotropic inelastic correction term $$A = \frac{1}{2}[F(D_{yy} - D_{zz})^2 + G(D_{zz} - D_{xx})^2 + H(D_{xx} - D_{yy})^2 + 2LD_{yz}^2 + 2MD_{zx}^2 + 2ND_{xy}^2]$$

and the anisotropic elastic correction term $$C = \underline{D} \cdot \underline{E}^{-1} \cdot \underline{D},$$

where F, G. H, L, M and N are the Hill parameters.

According to a preferred configuration of the method, the equation according to the modified Neuber rule is solved with an iterative process, in particular a Newton iteration.

According to the principles of the present invention, the method is preferably used for determining the service life of gas turbine components under cyclic loading.

DETAILED DESCRIPTION OF THE PREFERRED EMBODIMENTS

The material model on which the invention is based is derived from a plastic potential:

$$\Omega = \frac{\alpha \sigma_0^2}{E_R n} \left( \frac{\sigma_{v,ep}^2}{\sigma_0^2} \right)^n \tag{1}$$

where
- $E_R$ is the 'reference' stiffness. $E_R$ is incorporated in order to obtain the formal similarity of the compilation of formulas to that of the known isotropic case. $E_R$ is expediently selected in the order of magnitude of the elastic constant of the material considered, e.g. $E_R = 100000$ Nmm$^{-2}$,
- $\Omega$ is the plastic potential of the material, from which the plastic strains are calculated by derivation with respect to the stresses,
- $\sigma_0$ is a 'reference' stress which is expediently selected in the order of magnitude of the yield point, and
- $\sigma_{v,ep}$ is an anisotropic equivalent stress (see below).

The plastic strains are then $$\varepsilon_{pl} = \frac{\partial \Omega}{\partial \underline{\sigma}_{ep}} \tag{2}$$

From the plastic potential $\Omega$, the plastic strains εpl are thus formed by partial derivation with respect to the stresses $\underline{\sigma}_{ep}$.

With equations (1) and (2)

$$\frac{\partial \Omega}{\partial \underline{\sigma}_{ep}} = \frac{\partial \sigma_{v,ep}^2}{\partial \underline{\sigma}_{ep}} \frac{\alpha}{E_R} \left( \frac{\sigma_{v,ep}^2}{\sigma_0^2} \right)^{n-1}. \tag{3}$$

$\sigma_{v,ep}$ is the (anisotropic) equivalent stress. In the present anisotropic case, the equivalent stress according to HILL can be used:

$$\sigma_{v,ep}^2 = \frac{1}{2}[F(\sigma_{yy} - \sigma_{zz})^2 + G(\sigma_{zz} - \sigma_{xx})^2 + H(\sigma_{xx} - \sigma_{yy})^2 + 2L\sigma_{yz}^2 + 2M\sigma_{zx}^2 + 2N\sigma_{xy}^2] \tag{4}$$

For the general case of an orthotropic material, six independent plastic material constants F, G, H as well as L, M and N (Hill constants) are to be taken into account. The special case with 1=F=G=H=3L=3M=3N produces the known von Mises equivalent stress for isotropic materials; the special case with two independent parameters F=G=H and L=M=N produces the formulation for cubic crystal symmetry, which is of interest here for single-crystal materials (e.g. CMSX-4).

The following is obtained from equation (3)

$$\varepsilon_{pl} = \varepsilon_v \frac{\partial \sigma_{v,ep}^2}{\partial \underline{\sigma}_{ep}} \tag{5}$$

with the 'direction vector'

$$\frac{\partial \sigma_{v,ep}^2}{\partial \underline{\sigma}_{ep}} = \begin{pmatrix} -G(\sigma_{zz} - \sigma_{xx}) + H(\sigma_{xx} - \sigma_{yy}) \\ F(\sigma_{yy} - \sigma_{zz}) - H(\sigma_{xx} - \sigma_{yy}) \\ -F(\sigma_{yy} - \sigma_{xx}) + G(\sigma_{zz} - \sigma_{xx}) \\ 2N\sigma_{xy} \\ 2M\sigma_{zx} \\ 2L\sigma_{yz} \end{pmatrix} \tag{6}$$

and the 'equivalent strain'

$$\varepsilon_v = \frac{\alpha}{E_R} \cdot \left( \frac{\sigma_{v,ep}^2}{\sigma_0^2} \right)^{n-1} \tag{7}$$

For the single-crystal materials of interest here with cubic symmetry, the linear-elastic material equation becomes $$\underline{E}^{-1} = \begin{pmatrix} 1/E & -v/E & -v/E & 0 & 0 & 0 \\ -v/E & 1/E & -v/E & 0 & 0 & 0 \\ -v/E & -v/E & 1/E & 0 & 0 & 0 \\ 0 & 0 & 0 & 1/G & 0 & 0 \\ 0 & 0 & 0 & 0 & 1/G & 0 \\ 0 & 0 & 0 & 0 & 0 & 1/G \end{pmatrix} \tag{8}$$

E, G and v are the three independent elastic material constants for cubically symmetric (single-crystal) materials.

The complete anisotropic Ramberg-Osgood material law, as a sum of the elastic and plastic strains, is $$\underline{\varepsilon}_{ep} = \underline{E}^{-1} \cdot \underline{\sigma}_{ep} + \frac{\partial \sigma_{v,ep}^2}{\partial \underline{\sigma}_{ep}} \frac{\alpha}{E_R} \left( \frac{\sigma_{v,ep}^2}{\sigma_0^2} \right)^{n-1} \quad (9)$$

In the variant of the Neuber rule used here, the work of deformation is equated with the linear-elastic quantities and the elastic-plastic quantities $$\underline{\sigma}^{*dev} \cdot \underline{\varepsilon}^*(\underline{\sigma}^{*dev}) = \underline{\sigma}_{ep}^{dev} \cdot \underline{\varepsilon}_{ep}(\underline{\sigma}^{dev}) \quad (10)$$

The elastic plastic strain $\underline{\varepsilon}_{ep}(\underline{\sigma}^{dev})$ is obtained from the Ramberg-Osgood equation for deviatoric quantities $$\underline{\varepsilon}_{ep}(\underline{\sigma}_{ep}^{dev}) = \underline{E}^{-1} \cdot \underline{\sigma}_{ep}^{dev} + \frac{\partial \sigma_{v,ep}^2}{\partial \underline{\sigma}_{ep}} \frac{\alpha}{E_R} \left( \frac{\sigma_{v,ep}^2}{\sigma_0^2} \right)^{n-1} \quad (11)$$

and the linear elastic strain $\underline{\varepsilon}^*(\underline{\sigma}^{*dev})$ is obtained from Hooke's law in the form $$\underline{\varepsilon}^*(\underline{\sigma}^{*dev}) = \underline{E}^{-1} \cdot \underline{\sigma}^{*dev} \quad (12)$$

The anisotropic Neuber rule is thus obtained $$\underline{\sigma}^{*dev} \underline{\varepsilon}^*(\underline{\sigma}^{*dev}) = \underline{\sigma}^{*dev} \underline{E}^{-1} \underline{\sigma}^{*dev} \quad (13)$$

$$= \underline{\sigma}_{ep}^{dev} \underline{E}^{-1} \underline{\sigma}_{ep}^{dev} + \underline{\sigma}_{ep}^{dev} \cdot \frac{\partial \sigma_{v,ep}^2}{\partial \sigma} \cdot \frac{\alpha}{E_R} \left( \frac{\sigma_{v,ep}^2}{\sigma_0^2} \right)^{n-1}$$

Here, it is assumed that the elastic plastic stresses are to be proportional to the elastic stresses (from the finite element calculation). Or, in other words, it is assumed that the direction of the stress in the stress space does not change when proceeding from the elastic stresses σ* to the estimated inelastic stresses. The 'direction vector' can be determined from $$\underline{\sigma}^{*dev} = \underline{D}\sqrt{\sigma^{*2}} \quad (14)$$

Now, for the inelastic (estimated) stresses, with the same direction vector $$\underline{\sigma}_{ep}^{dev} = \underline{D}\sqrt{\sigma_{ep}^2} \quad (15)$$

For the elastic stresses, this immediately gives $$\underline{\sigma}^{*dev} \underline{E}^{-1} \underline{\sigma}^{*dev} \underline{D} \cdot \underline{E}^{-1} \cdot \underline{D} \sigma^{*2} = C\sigma^{*2} \quad (16)$$

and for the inelastic stresses $$\underline{\sigma}^{dev} \underline{E}^{-1} \underline{\sigma}^{dev} = \underline{D} \cdot \underline{E}^{-1} \cdot \underline{D} \sigma^2 = C\sigma^2 \quad (17)$$

For the elastoplastic equivalent stress $$\sigma_{v,ep}^2 = \frac{1}{2}[F(D_{yy} - D_{zz})^2 + G(D_{zz} - D_{xx})^2 + \quad (18)$$
$$H(D_{xx} - D_{yy})^2 + 2LD_{yz}^2 + 2MD_{zx}^2 + 2ND_{xy}^2]\sigma_{ep}^2$$
$$= A\sigma_{ep}^2$$

Thus equation (13) can also be represented in the form $$\sigma^{*2} = \sigma_{ep}^2 \left( 1 + \frac{A}{C} \frac{\alpha}{E_R} \left( \frac{A\sigma_{ep}^2}{\sigma_0^2} \right)^{n-1} \right) \quad (19)$$

with the anisotropic inelastic correction term $$A = \frac{1}{2}[F(D_{yy} - D_{zz})^2 + G(D_{zz} - D_{xx})^2 + \quad (20)$$
$$H(D_{xx} - D_{yy})^2 + 2LD_{yz}^2 + 2MD_{zx}^2 + 2ND_{xy}^2]$$

and the anisotropic elastic correction term $$C = \underline{D} \cdot \underline{E}^{-1} \cdot \underline{D} \quad (21)$$

The abovementioned equation (19) for $\sigma^2_{ep}$, as in the case of the 'classic' Neuber rule, can be solved with an iterative process (Newton iteration). If $\sigma^2_{ep}$ is determined, the elastoplastic stress vector can be calculated immediately by means of $\underline{D}$.

To recalculate the 'linear' results of the finite element calculations, it is expedient to implement the abovementioned procedure in a post-processing procedure which reads the 'linear' data for the strains and stresses from result files for the FE programs and further processes them into the sought-after inelastic results. In the case of the isotropic Neuber rule, this is prior art. It is very easy to extend this to the anisotropic Neuber rule described here by incorporating the two abovementioned 'correction factors' in the iteration procedure.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method of determining the elastoplastic behavior of components at high temperatures, the method comprising:
   determining the linear-elastic behavior; and
   determining the inelastic behavior based on the determined linear-elastic by using a Neuber rule;
   wherein, to take into account anisotropic characteristics of the components,, said Neuber rule comprises a modified anisotropic Neuber rule of the form $$\underline{\sigma}^{*dev} \underline{\varepsilon}^*(\underline{\sigma}^{*dev}) = \underline{\sigma}^{*dev} \underline{E}^{-1} \underline{\sigma}^{*dev} = \underline{\sigma}_{ep}^{dev} \underline{E}^{-1} \underline{\sigma}_{ep}^{dev} +$$

$$\underline{\sigma}_{ep}^{dev} \cdot \frac{\partial \sigma_{v,ep}^2}{\partial \sigma} \cdot \frac{\alpha}{E_R} \left( \frac{\sigma_{v,ep}^2}{\sigma_0^2} \right)^{n-1}$$

wherein
$\underline{\sigma}^{*dev}$=deviator of the determined linear stress
$\underline{\varepsilon}(\underline{\sigma}^{*dev})$=determined linear strain
$\underline{\sigma}_{ep}^{dev}$=estimated inelastic stress,
$\sigma_{v,ep}$=Hill elastic-plastic equivalent stress,
$\underline{E}^{-1}$=inverse stiffness matrix,
$E_R$=reference stiffness,
$\sigma_0$=reference stress, and
$\alpha$, n=constants.

2. The method as claimed in claim 1, characterized in that, for the quantities $\underline{\sigma}^{*dev}$ and $\underline{\sigma}^{dev}_{ep}$, the following equations are used:

$$\underline{\sigma}^{*dev} = \underline{D} \cdot \sqrt{\sigma^{*2}}$$

and $$\sigma^{dev}_{ep} = \underline{D} \cdot \sqrt{\sigma^2_{ep}}$$

where $\underline{D}$ designates a direction vector of the length 1 with deviatoric characteristics, and in that the modified Neuber rule is used in the form $$\sigma^{*2} = \sigma^2_{ep}\left(1 + \frac{A}{C}\frac{\alpha}{E_R}\left(\frac{A\sigma^2_{ep}}{\sigma^2_0}\right)^{n-1}\right)$$

with the anisotropic inelastic correction term $$A = \frac{1}{2}[F(D_{yy} - D_{zz})^2 + G(D_{zz} - D_{xx})^2 +$$
$$H(D_{xx} - D_{yy})^2 + 2LD^2_{yz} + 2MD^2_{zx} + 2ND^2_{xy}]$$

and the anisotropic elastic correction term $$C = \underline{D} \cdot \underline{E}^{-1} \cdot \underline{D}$$

and wherein the Hill parameters are designated by F, G, H, L, M, and N.

3. The method as claimed in claim 2, further comprising:

solving the equation according to the modified Neuber rule with an iterative process.

4. The method as claimed in claim 1, comprising:

determining the service life of gas turbine components under cyclic loading.

5. The method as claimed in claim 1, wherein said components comprise components of a gas turbine plant.

6. The method as claimed in claim 1, wherein said components comprise single-crystalline materials.

7. The method as claimed in claim 3, wherein said iterative process comprises a Newton iteration.

* * * * *